US00PP19489P2

(12) United States Plant Patent
Zary

(10) Patent No.: US PP19,489 P2
(45) Date of Patent: Nov. 25, 2008

(54) SHRUB ROSE NAMED 'JACZORBA'

(50) Latin Name: *Rosa hybrida*
Varietal Denomination: JACzorba

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,253

(22) Filed: Nov. 28, 2007

(51) Int. Cl.
*A01H 5/00* (2006.01)

(52) U.S. Cl. ..... Plt./105
(58) Field of Classification Search ..... Plt./105
See application file for complete search history.

*Primary Examiner*—Kent L. Bell
*Assistant Examiner*—Georgia Helmer
(74) *Attorney, Agent, or Firm*—Klarquist Sparkman LLP

(57) ABSTRACT

Shrub rose plant having flowers with fruity fragrance; vigorous, upright growth; dark green healthy foliage; distinctive striped petals; and ability to propagate and grow vigorously on its own roots.

1 Drawing Sheet

Genus and Species: *Rosa hybrida.*
Variety Denomination: 'JACzorba'.

Origin of the Invention

The present invention relates to a new and distinct variety of a shrub rose plant named 'JACzorba' which was originated by me by crossing an unnamed apricot-yellow floribunda variety (unpatented, seed parent) with an unnamed striped red and white shrub rose (unpatented, pollen parent). The parentage of the seed parent is 'JACrun' (unpatented)× 'JACjem', (U.S. Plant Pat. No. 6,001). The parentage of the pollen parent is an unnamed yellow floribunda× 'MACminmo' (U.S. Plant Pat. No. 7,319).

Background of the Invention

The primary objective of this breeding was to produce a new shrub rose variety having the fragrance and healthy foliage of the unnamed female parent combined with the striped coloration of the unnamed male parent.

Brief Summary of the Invention

The objective was substantially achieved, along with other desirable improvements, as evidenced by the following unique combination of characteristics that are outstanding in the new variety and that distinguish it from its parents, as well as from all other varieties of which I am aware:

1. Fruit fragrance.
2. Vigorous, upright growth.
3. Dark green, healthy foliage.
4. Distinctive striped petals.
5. Ability to propagate and grow vigorously on its own roots.

Asexual reproduction of this new variety by cuttings, as performed as Wasco, Calif., shows that the foregoing characteristics and distinctions come true to form and are established and transmitted through succeeding propagations.

Comparison with Parents

'JACzorba' differs from the unnamed female (seed) parent in flower color (apricot-yellow) for seed parent versus orange-red and yellow stripe for 'JACzorba'). 'JACzorba' differs from the unnamed male (pollen) parent in fragrance (male parent has none), in clustering ability (male parent produces single flowers versus large clusters for the varity 'JACzorba').

Comparison with Similar Variety

The closest variety to 'JACzorba' known to the inventor is 'WEKcalroc' (U.S. Pat. No. 10,334). 'JACzorba' differs in petal count ('JACzorba' typically has 15–20 petals versus 30–35 petals for 'WEKcalroc') and in plant habit ('JACzorba' is shrubby typically growing to 150 cm tall when mature versus 80–100 cm for 'WEKcalroc').

Brief Description of the Illustration

The accompanying illustration shows typical specimens of the vegetative growth and flowers of this new variety in different stages of development, depicted in color as nearly true as it is reasonably possible to make the same in a color illustration of this character.

Detailed Botanical Description

The following is a detailed description of my new rose cultivar with color descriptions using terminology in accordance with the Royal Horticultural Society (London) Colour Chart© 2001, except where ordinary dictionary significance of color is indicated.

Parentage:

*Seed parent.*—Unnamed apricot-yellow floribunda variety (not patented). Parentage of seed parent is 'JACrun' (unpatented)×'JACjem' (U.S. Plant Pat. No. 5,001).

*Pollen parent.*—Unnamed striped red and white shrub rose (unpatented). Parentage of pollen parent is unnamed yellow floridbunda (unpatented)× 'MACminmo' (U.S. Plant Pat. No. 7,319).

FLOWER

Observations made from January 2006 to October 2007 from plants that were four years of age of completion of observation, grown in a garden environment at Somis, Calif.

Blooming Habit: Continuous.

Bud:

*Size.*—About 2.5–3.0 cm and 2.0–2.5 cm in diameter when the petals start to unfurl.

*Form.*—The bud form is potted ovoid.

*Color.*—When sepals first divide, bud color is Red Group 43B striped with Yellow Group 11A. When half blown, the upper sides of the petals are Red Group 43B striped with Yellow Group 10B and the lower sides of the petals are Red Group 43B striped with Yellow Group 11A.

*Sepals.*—Color: Upper surface: Green Group 138B. Lower surface: Yellow-Green Group 144B. Length: 26–30 mm. Width: 5–9 mm. Shape: Subulate. Surface: Upper: Hoary, Lower: Smooth. There are three normally appendaged sepals. There are two unappendaged sepals with glandular edges.

*Receptacles.*—Color: Yellow-Green Group 144B. Shape: Apple. Size: About 5–7 mm long×6–8 mm in wide. Surface: Smooth.

*Peduncle.*—Length: Medium, average about 6–8 cm. Surface: Prickly (very small prickles), glandular. Color: Yellow-Green Group 144B. Strength: Stiff, erect.

Bloom:

*Size.*—Medium. Average open diameter is about 6–8 cm.

*Borne.*—Several together in clusters of 15–20 blooms having flat shape.

*Stems.*—Strength: Normal. Average length is about 40–50 cm with a diameter of 6–8 mm.

*Form.*—When first open: Cupped then flat. Permanence: Flattens with age.

*Petalage.*—Number of petals under normal conditions: 15–20. Color: The upper sides of the petals are Red Group 43B striped with Yellow Group 10B. The reverse sides of the petals are Red Group 43B striped with Yellow Group 11A. The base of the petals has Yellow Group 13A. The major color on the upper sides is Red Group 43B striped with Yellow Group 10B.

*Variegations.*—Described above.

*Discoloration.*—The general tonality at the end of the first day: Red Group 43B stripped with Yellow Group 10B. At the end of the third day: Changes to Red Group 48C striped with Yellow Group 11C. Fades to Red Group 48D striped with Yellow Group 11D by day five.

*Fragrance.*—Moderate. Fruity.

Petals:

*Thickness.*—Medium.

*Surface texture.*—Smooth.

*Shape.*—Obovate.

*Margin.*—Entire.

*Apex shape.*—Obtuse.

*Base shape.*—Obcordate.

*Form.*—Tips slightly recurved.

*Arrangement.*—Imbricated.

*Petaloids.*—Number: 3–5. Color: Red Group 43B striped with Yellow Group 10B.

*Persistence.*—Petals drop off cleanly before drying.

*Lastingness.*—On the plant: Fair (about 3–5 days). As a cut flower: Fair (about 5–7 days).

Reproductive Parts:

*Stamens: Number:* 90–110. Length: 8–12 mm. Anthers: Length: 2–3 mm. Color: Yellow-Orange Group 21B. Arrangement: Regular around styles. Filaments: Color: Yellow-Orange Group 15B. Length: 5–10 mm. Pollen: Color: Yellow-Orange Group 21A.

*Pistils.*—Number: 60–80. Length: 6–7 mm. Styles: Color: Bottom two-thirds, Green White Group 157B, top one-third Red Group 46D. Length: 5–6 mm. Stigmas: Color: Greyed-Yellow Group 161B. Length: 1 mm.

*Hips.*—None observed, female sterile.

PLANT

*Form.*—Bush, shrub.

*Growth.*—Vigorous.

*Age to maturity.*—Two years.

*Mature plant.*—Height: 150 cm. Width: 100 cm.

*Rootstock.*—Own root.

Foliage: Number of leaflets on normal mid-stem leaves: 5 or 7.

*Size.*—Large. About 130 mm long×100 mm wide.

*Color.*—New foliage: Upper side: Greyed-Purple Group 187A. Lower side: Greyed-Purple Group 183A. Old foliage: Upper side: Green Group 139A. Lower side: Green Group 137B.

Leaflets:

*Size.*—About 45 mm long×30 mm wide.

*Shape.*—Oval.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 147C.

*Petiole rachis.*—Color: Yellow-Green Group 147C. Underside: Smooth with occasional prickles.

*Auricles.*—None observed.

*Stipules.*—Length: 20 mm, smooth with some glands.

*Disease resistance.*—Resistant to mildew and rust and susceptible to blackspot under normal growing conditions.

*Pest resistance.*—None observed.

*Vein color.*—Green Group 139A.

*Venation pattern.*—Reticulate.

Wood:

*New wood.*—Color: Yellow-Green Group 146D, overlaid with Greyed-Purple Group 183A. Bark: Smooth.

*Old wood.*—Color: Green Group 137B that is often overlaid with Greyed-Purple Group 183A. Bark: Smooth.

Prickles:

*Quantity.*—Ordinary, on main canes from base: 15–17 per 15 cm of wood. Ordinary, on laterals from main canes: 9–12 per 15 cm of wood.

*Form.*—Hooked downward.

*Length.*—7–8 mm.

*Color when young.*—Greyed-Red Group 183A.

*Color when mature.*—Greyed-Orange Group 166D.

Small Prickles:

*Quantity.*—On main stalks: Few. 7–9 per 15 cm of wood. On laterals: None observed.

*Color when young.*—Greyed-Red Group 183A.

*Color when mature.*—Greyed-Orange Group 166D.

I claim:

1. A new and distinct variety of shrub rose plant, substantially as herein shown and described, characterized particularly by its fruity fragrance; vigorous, upright growth; dark green, healthy foliage; distinctive striped petals; and ability to propagate and grow vigorously on its own roots.

* * * * *

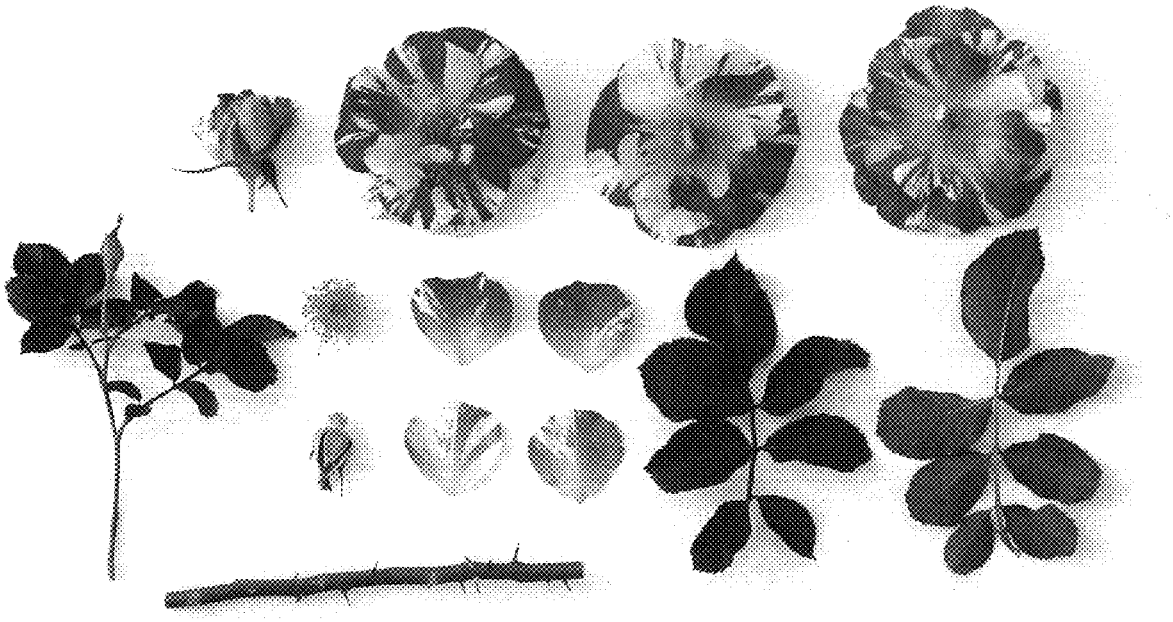
JACzorba

UNITED STATES PATENT AND TRADEMARK OFFICE

CERTIFICATE OF CORRECTION

PATENT NO. : PP 19,489 P2
APPLICATION NO. : 11/998253
DATED : November 25, 2008
INVENTOR(S) : Keith W. Zary It is certified that error appears in the above-identified patent and that said Letters Patent is hereby corrected as shown below:

In the Specification:

Column 1, line 12, "Plant Pat. No. 6,001" should be --Plant Pat. No. 5,001--.
Column 1, line 31, "Fruit" should be --Fruity--.
Column 2, line 3, "(apricot-yellow) for" should be --(apricot-yellow for--.
Column 2, line 41, "floridbunda" should be --floribunda--.
Column 3, line 3, "age of completion" should be --age at completion--.
Column 3, line 10, "potted" should be --pointed--.
Column 3, line 45, "stripped" should be --striped--.

Signed and Sealed this

Ninth Day of June, 2009

JOHN DOLL
*Acting Director of the United States Patent and Trademark Office*